US011817217B2

United States Patent
Sharma et al.

(10) Patent No.: US 11,817,217 B2
(45) Date of Patent: Nov. 14, 2023

(54) DISCRIMINATING FEATURES BASED SEPSIS PREDICTION

(71) Applicant: Tata Consultancy Services Limited, Mumbai (IN)

(72) Inventors: Varsha Sharma, Kolkata (IN); Chirayata Bhattacharyya, Kolkata (IN); Tanuka Bhattacharjee, Kolkata (IN); Murali Poduval, Mumbai (IN); Sundeep Khandelwal, Noida (IN); Anirban Dutta Choudhury, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 389 days.

(21) Appl. No.: 17/117,375

(22) Filed: Dec. 10, 2020

(65) Prior Publication Data

US 2021/0315511 A1 Oct. 14, 2021

(30) Foreign Application Priority Data

Mar. 21, 2020 (IN) .............................. 202021012285

(51) Int. Cl.
*G16H 50/30* (2018.01)
*G16H 50/70* (2018.01)
(Continued)

(52) U.S. Cl.
CPC ............. *G16H 50/30* (2018.01); *A61B 5/412* (2013.01); *A61B 5/7267* (2013.01); *G06F 18/2113* (2023.01); *G06F 18/2132* (2023.01); *G06F 18/2148* (2023.01); *G06F 18/2193* (2023.01); *G06N 20/00* (2019.01); *G06V 20/698* (2022.01); *G16H 40/67* (2018.01); *G16H 50/70* (2018.01)

(58) Field of Classification Search
CPC ........ G16H 50/20; G16H 50/30; G16H 50/70; G16H 10/60
See application file for complete search history.

(56) References Cited

U.S. PATENT DOCUMENTS

| 2019/0164648 A1* | 5/2019 | Conroy .................... G06N 7/01 |
| 2020/0005900 A1 | 1/2020 | Cha et al. |
| 2021/0087632 A1* | 3/2021 | Garrett ................. C12Q 1/6888 |

FOREIGN PATENT DOCUMENTS

WO WO-2021134027 A1 * 7/2021 ......... A61B 5/14546

OTHER PUBLICATIONS

Cambiaghi, Alice, et al. "An innovative approach for the integration of proteomics and metabolomics data in severe septic shock patients stratified for mortality." Scientific Reports 8.1 (2018): 6681. (Year: 2018).*

(Continued)

*Primary Examiner* — Jason B Dunham
*Assistant Examiner* — Constantine Siozopoulos
(74) *Attorney, Agent, or Firm* — Finnegan, Henderson, Farabow, Garrett & Dunner, LLP

(57) ABSTRACT

Sepsis is one of the most prevalent causes of mortality in Intensive Care Units (ICUs) and delayed treatment is associated with increase in death and financial burden. There is no single laboratory test or clinical sign that by itself can be considered diagnostic of sepsis. The present disclosure provides discriminating domain specific continuous and categorical features that can reliably classify a subject being monitored into a sepsis class or a normal class. A combination of physiological parameters, laboratory parameters and demographic details are used to extract the discriminating features. Even though the parameters may be sporadic in nature, the systems and methods of the present disclosure make use of a sliding time window to generate continuous features that capture the trend in the sporadic data; and a binning approach to generate categorical features to discriminate deviation from the normal class and facilitate timely treatment.

17 Claims, 11 Drawing Sheets

(51) Int. Cl.
*G16H 40/67* (2018.01)
*G06N 20/00* (2019.01)
*A61B 5/00* (2006.01)
*G06V 20/69* (2022.01)
*G06F 18/2113* (2023.01)
*G06F 18/2132* (2023.01)
*G06F 18/214* (2023.01)
*G06F 18/21* (2023.01)

(56) References Cited

OTHER PUBLICATIONS

Bloch, Eli et al., "Machine Learning Models for Analysis of Vital Signs Dynamics: A Case for Sepsis Onset Prediction", Journal of Healthcare Engineering, Nov. 2019, NCBI, http://downloads.hindawi.com/journals/jhe/2019/5930379.pdf.

Masud, Mohammad M. et al., "A Framework for Utilizing Lab Test Results for Clinical Prediction of ICU Patients", Artificial Intelligence, Nov. 2018, AAAI, https://aaai.org/ocs/index.php/WS/AAAIW18/paper/download/16622/15605.

Guillen, Joseph et al., "Predictive models for severe sepsis in adult ICU patients", Systems and Information Engineering Design Symposium, Apr. 2015, IEEE, https://ieeexplore.ieee.org/document/7116970.

Abromavicius, Vytautas et al., "Sepsis Prediction Model Based on Vital Signs Related Features", Computing in Cardiology (CinC), Sep. 2019, IEEE, https://www.researchgate.net/publication/338627179_Sepsis_Prediction_Model_Based_on_Vital_Signs_Related_Features.

* cited by examiner

DISCRIMINATING FEATURES BASED SEPSIS PREDICTION

PRIORITY CLAIM

This U.S. patent application claims priority under 35 U.S.C. § 119 to: Indian Patent Application No. 202021012285, filed on 21 Mar. 2020. The entire contents of the aforementioned application are incorporated herein by reference.

TECHNICAL FIELD

The disclosure herein generally relates to sepsis prediction, and, more particularly, to systems and methods for extracting discriminating features for predicting sepsis in a timely manner.

BACKGROUND

Sepsis is a life-threatening condition that is caused by the body's response to an infection. The body normally releases some chemicals into the bloodstream to fight an infection. When sepsis occurs, the body's response to these chemicals go out of balance and trigger certain changes that damage multiple organs in the body. People can get affected by sepsis at any time, but those staying in Intensive Care Unit (ICU) are more susceptible to contract it. Sepsis develops gradually and escalates to catastrophic multi-organ failure with a very high risk of mortality. However, no single laboratory test or clinical sign, by itself, can be considered diagnostic of sepsis. Research reveals that mortality from severe sepsis and septic shock improves by 7.6 per hour with early and appropriate administration of antibiotics. Standard routine blood cultures to detect sepsis can take 6 hours to 5 days to grow an organism to detectable levels. Additional time is required to identify the organism and test for appropriate antibiotic susceptibility (24-48 hours). Thus, reliable means of annotated early prediction of sepsis using available lab data and vitals is a critical problem.

SUMMARY

Embodiments of the present disclosure present technological improvements as solutions to one or more of the above-mentioned technical problems recognized by the inventors in conventional systems.

In an aspect, there is provided a processor implemented method comprising the steps of: receiving, via one or more hardware processors, test signals corresponding to one or more parameters, wherein the one or more parameters include physiological parameters, laboratory parameters and demographic parameters, and wherein the test signals are obtained periodically from a subject being monitored; extracting, via the one or more hardware processors, a plurality of discriminating features from the received test signals, wherein the plurality of discriminating features is a combination of continuous features and categorical features extracted during a training phase of at least one classifier; normalizing, via the one or more hardware processors, the extracted plurality of discriminating features using stored values of standard deviation and mean associated with the one or more parameters from the training phase, wherein the normalizing is performed across sliding time windows; ranking, via the one or more hardware processors, the normalized extracted plurality of discriminating features using a Minimum Redundancy Maximum Relevance (MRMR) method to identify a subset of the plurality of discriminating features such that the subset is representative of a sepsis condition in the subject being monitored; and predicting, via the one or more hardware processors, a classification of the subject being monitored into one of a sepsis class and a normal class based on the identified subset using the at least one classifier trained during the training phase.

In another aspect, there is provided a system comprising: one or more data storage devices operatively coupled to one or more hardware processors and configured to store instructions configured for execution via the one or more hardware processors to: receive test signals corresponding to one or more parameters, wherein the one or more parameters include physiological parameters, laboratory parameters and demographic parameters, and wherein the test signals are obtained periodically from a subject being monitored; extract a plurality of discriminating features from the received test signals, wherein the plurality of discriminating features is a combination of continuous features and categorical features extracted during a training phase of at least one classifier; normalize the extracted plurality of discriminating features using stored values of standard deviation and mean associated with the one or more parameters from the training phase, wherein the normalizing is performed across sliding time windows; rank the normalized extracted plurality of discriminating features using a Minimum Redundancy Maximum Relevance (MRMR) method to identify a subset of the plurality of discriminating features such that the subset is representative of a sepsis condition in the subject being monitored; and predict a classification of the subject being monitored into one of a sepsis class and a normal class based on the identified subset using the at least one classifier trained during the training phase.

In yet another aspect, there is provided a computer program product comprising a non-transitory computer readable medium having a computer readable program embodied therein, wherein the computer readable program, when executed on a computing device, causes the computing device to: receive test signals corresponding to one or more parameters, wherein the one or more parameters include physiological parameters, laboratory parameters and demographic parameters, and wherein the test signals are obtained periodically from a subject being monitored; extract a plurality of discriminating features from the received test signals, wherein the plurality of discriminating features is a combination of continuous features and categorical features extracted during a training phase of at least one classifier; normalize the extracted plurality of discriminating features using stored values of standard deviation and mean associated with the one or more parameters from the training phase, wherein the normalizing is performed across sliding time windows; rank the normalized extracted plurality of discriminating features using a Minimum Redundancy Maximum Relevance (MRMR) method to identify a subset of the plurality of discriminating features such that the subset is representative of a sepsis condition in the subject being monitored; and predict a classification of the subject being monitored into one of a sepsis class and a normal class based on the identified subset using the at least one classifier trained during the training phase.

In accordance with an embodiment of the present disclosure, the one or more hardware processors are configured to perform, during the training phase of the at least one classifier, steps comprising: receiving training signals corresponding to the one or more parameters, and wherein the training signals are obtained periodically from a plurality of subjects; extracting the plurality of discriminating features from the received training signals; normalizing the extracted plurality of discriminating features using values of standard deviation and mean associated with the one or more parameters, wherein the normalizing is performed across the plurality of subjects; ranking the normalized extracted plurality of discriminating features using the MRMR method to identify the subset of the plurality of discriminating features; under-sampling a majority class to balance the sepsis class and the normal class in the received training signals; and training the at least one classifier using the identified subset corresponding to the balanced sepsis class and the normal class.

In accordance with an embodiment of the present disclosure, the one or more hardware processors are configured to preprocess the received test signals by imputing missing data therein before extracting the plurality of discriminating features from the received test signals.

In accordance with an embodiment of the present disclosure, the one or more hardware processors are configured to preprocess the received training signals by imputing missing data therein before extracting the plurality of discriminating features from the received training signals.

In accordance with an embodiment of the present disclosure, the at least one classifier includes at least one of a Random Forest (RF) model and an Adaptive Logistic Regression of Ensemble learning (LB) model.

In accordance with an embodiment of the present disclosure, the (i) the continuous features associated with the one or more parameters being the physiological parameters and the laboratory parameters over an empirically determined sliding time window (i hours) including: a) count of valid data records associated with the one or more parameters; b) count of out of range data records associated with the one or more parameters; c) difference between a value associated with the one or more parameters at an $i^{th}$ hour and an $(i-1)^{th}$ hour; d) difference between a value associated with the one or more parameters at the $i^{th}$ hour and a mean of past $(i-1)$ hours; and e) difference between a value associated with the one or more parameters at the $i^{th}$ hour and a variance of the past $(i-1)$ hours; (ii) the categorical features by using a binning approach on the one or more parameters being the physiological parameters and the laboratory parameters including: a) Category; b) Upper limit (UL); c) Lower limit (LL); and d) One hot dummy encoding; (iii) the categorical features corresponding to demography including: a) Current hospital admission duration; b) Intensive Care Unit (ICU) type; c) Gender; d) Age binned in empirically determined categories of ranges of the age; e) Current ICU stay duration binned in steps of empirically determined hours; f) The LL of current ICU stay duration; g) The UL of current ICU stay duration; h) The LL of age; and i) The UL of age; (iv) the categorical features corresponding to a sepsis domain including: a) National Early Warning Score (NEWS); b) Modified Early Warning Score (MEWS); and c) Acute Physiology and Chronic Health Evaluation II (APACHE II).

In accordance with an embodiment of the present disclosure, the one or more hardware processors are configured to obtain a final class of the subject being monitored by fusing predictions by the RF model and the LB model using one or more logical operations.

In accordance with an embodiment of the present disclosure, the one or more hardware processors are configured to administer antibiotics to the subject being predicted as belonging to the class sepsis.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
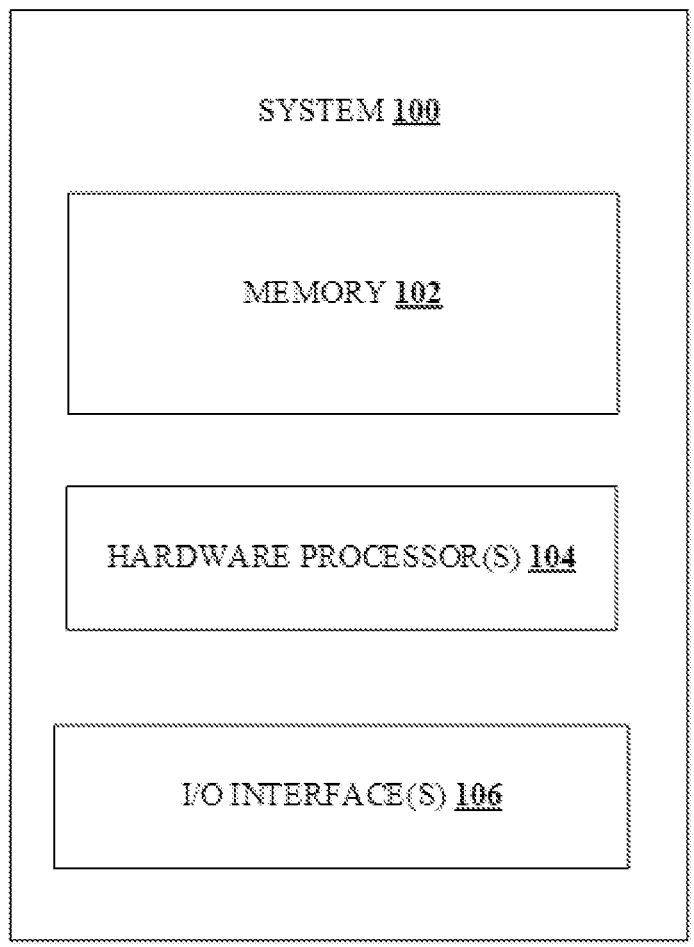
FIG. 1 illustrates an exemplary block diagram of a system for discriminating features based sepsis prediction, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Sepsis is one of the leading life-threatening bacterial and viral infections that often turns fatal if not detected and treated in time. Sepsis refers to the syndrome wherein a previously known or unknown infection leads to immune system override and rapid progression to multi-organ failure. People can get affected by sepsis at any time, but those staying in an Intensive Care Unit (ICU) are more susceptible to contract it. Sepsis develops gradually and escalates to catastrophic multi-organ failure with a very high risk of mortality. However, no single laboratory test or clinical sign, by itself can be considered diagnostic of sepsis. The diagnosis requires great clinical acumen and alertness, in combination with an astute analysis of laboratory results and physiological parameters like heart rate, mean arterial pressure and respiratory rate. A high index of suspicion coupled with known scores enables a clinician to institute treatment with antibiotics in time to save life. High risk populations especially include those with multiple comorbidities like diabetes and heart disease, increasing age and intensive care admissions. Research reveals that mortality from severe sepsis and septic shock improves by 7.6% per hour with early and appropriate administration of antibiotics.

Use of standard culture techniques for detection and isolation of pathogenic organisms from a sterile body fluid specimen is still considered the "gold standard" for diagnosis of infection and sepsis. Routine blood cultures by this standard to detect sepsis can take 6 hours to 5 days to grow an organism to detectable levels and additional time is required to identify the organism and test for appropriate antibiotic susceptibility (24-48 hours). Various scoring systems include Sequential Organ Failure Assessment (SOFA) Score, Systematic Inflammatory Response Syndrome (SIRS) criteria and Simplified Acute Physiology Score (SAPS II). These methods result in a well-structured tabulation of vital signs and lab data to generate indicative scores and risk assessments. However, they do not analyze trends in patient data or correlation between measurements to aid sepsis prediction. It is critical to have a reliable means of annotated early prediction of sepsis using available data which is practically sporadic in nature. Applicant has addressed these problems by providing systems and methods for discriminating features based sepsis prediction.

In the context of the present disclosure, the expression 'normal' may be understood to represent 'non-sepsis' condition. Likewise, the expressions 'subject' and 'patient' may be used interchangeably.

Referring now to the drawings, and more particularly to FIG. 1 through FIG. 10, where similar reference characters denote corresponding features consistently throughout the figures, there are shown preferred embodiments and these embodiments are described in the context of the following exemplary system and/or method.

FIG. 1 illustrates an exemplary block diagram of a system 100 for discriminating features based sepsis prediction, in accordance with some embodiments of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
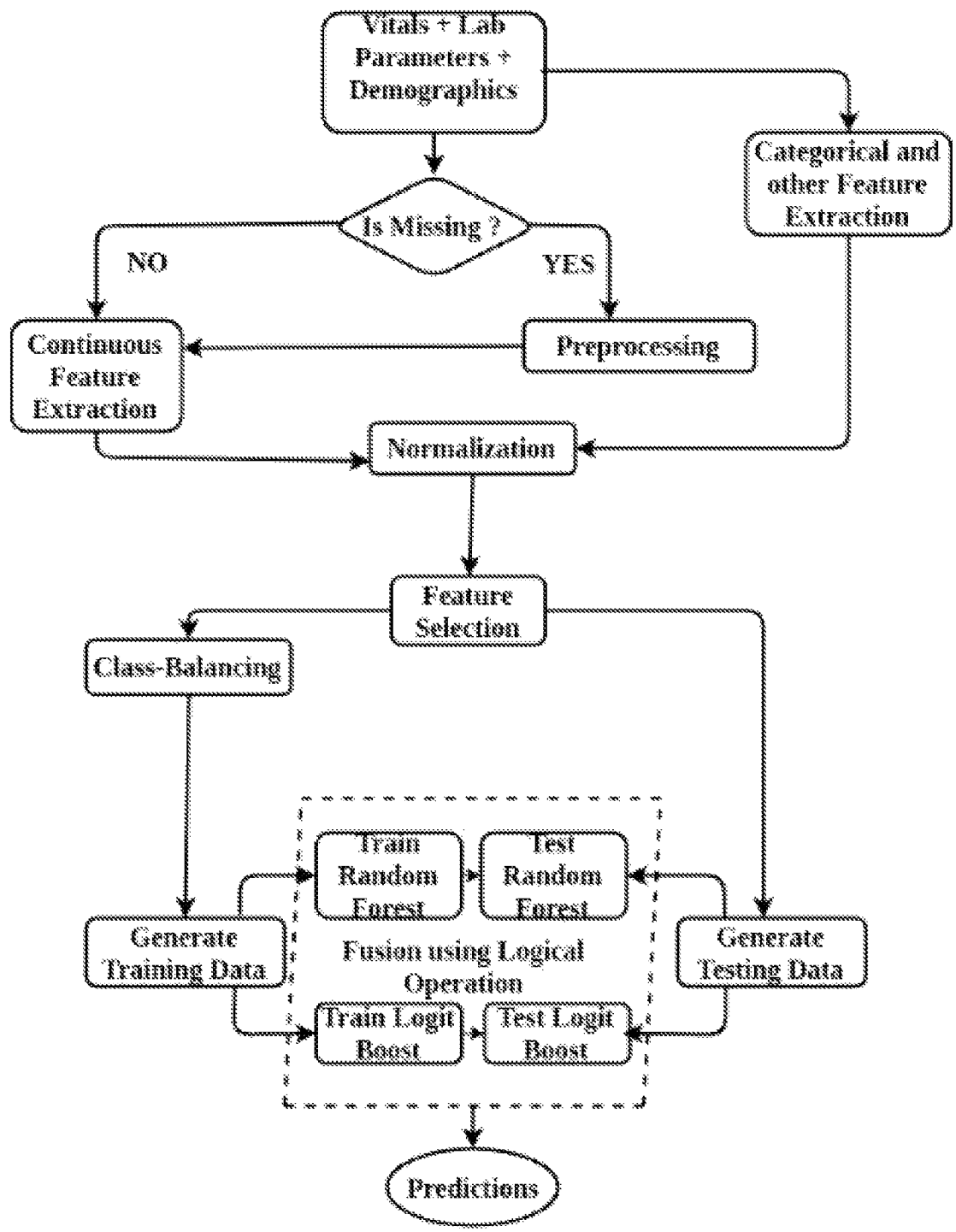
FIG. 2 illustrates a high-level flow chart of a method for discriminating features based sepsis prediction, in accordance with some embodiments of the present disclosure.
Figure 3A:
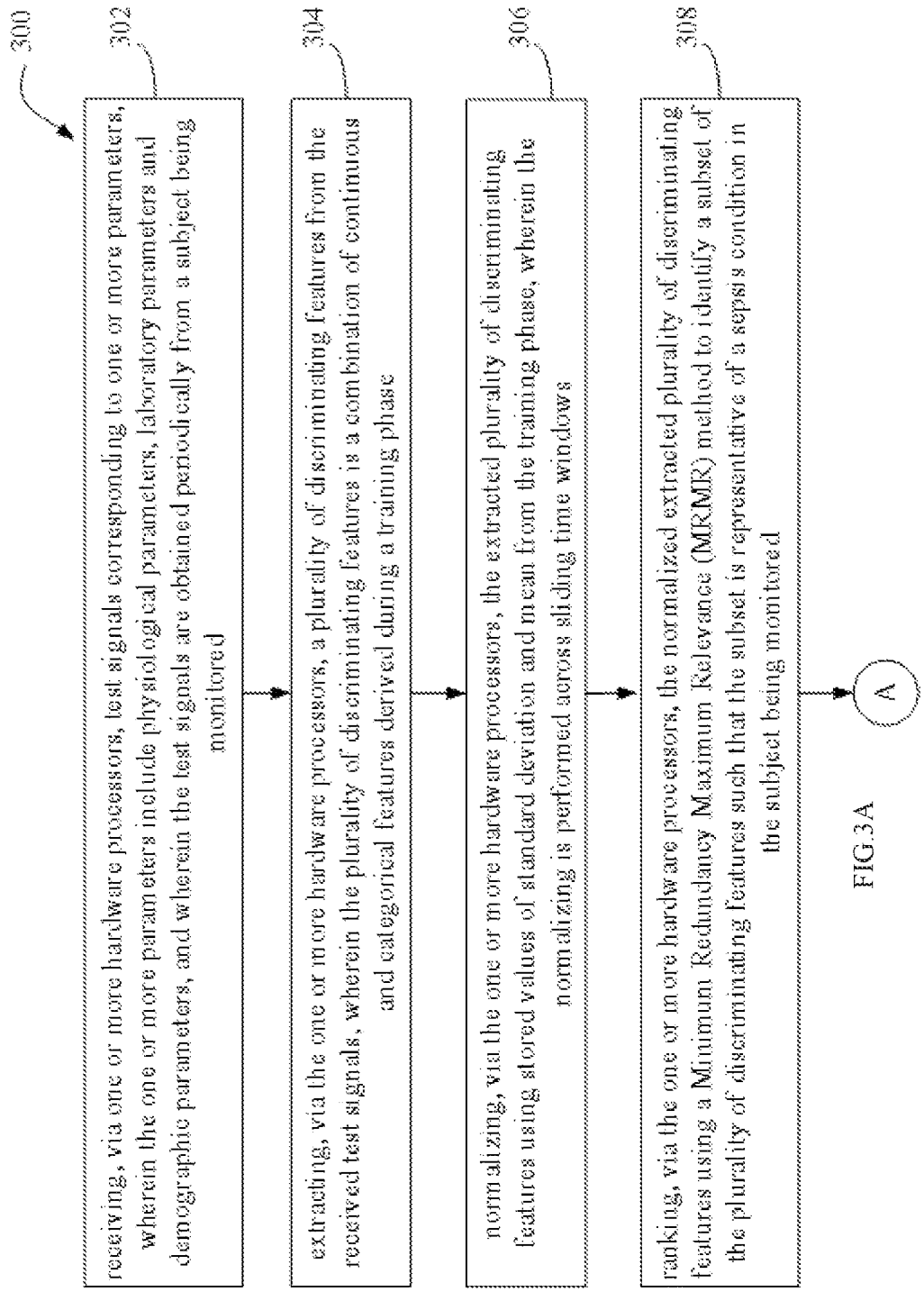
FIG. 3A and FIG. 3B illustrate an exemplary flow diagram of a computer implemented method for discriminating features based sepsis prediction, in accordance with some embodiments of the present disclosure.
Figure 3B:
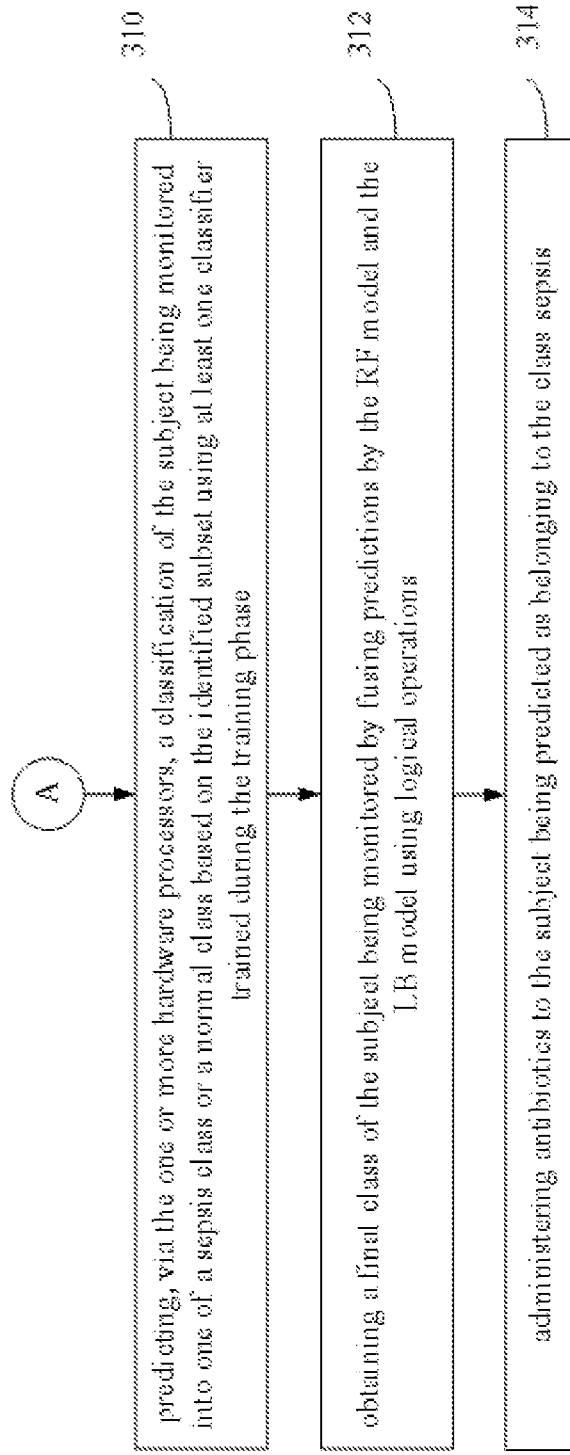

FIG. 2 illustrates a high-level flow chart of a method for discriminating features based sepsis prediction, in accordance with some embodiments of the present disclosure. FIG. 3A and FIG. 3B illustrate an exemplary flow diagram of a computer implemented method 300 for discriminating features based sepsis prediction, in accordance with some embodiments of the present disclosure. In an embodiment, the system 100 includes one or more data storage devices or memory 102 operatively coupled to the one or more processors 104 and is configured to store instructions configured for execution of steps of the method 300 by the one or more processors 104. The steps of the method 300 will now be explained in detail with reference to the components of the system 100 of FIG. 1 and the high-level flow chart of FIG. 2. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In an embodiment of the present disclosure, the one or more processors 104, are configured to receive, at step 302, test signals corresponding to one or more parameters, wherein the one or more parameters include physiological parameters, laboratory parameters and demographic parameters. The test signals are obtained periodically (typically hourly) from a subject being monitored. In most cases, the subject is housed in an Intensive Care Unit (ICU).

The physiological parameters are typically associated with vital signals (Vitals in FIG. 2) such as Heart rate (HR), Oxygen saturation (O2sat), temperature, Systolic Blood Pressure (SBP), Mean Arterial Pressure (MAP), Diastolic Blood Pressure (DBP), Respiration Rate (RR or Resp) and end-tidal Carbon dioxide (EtCO2). The laboratory parameters (Lab parameters in FIG. 2) typically include Platelets, Fibrinogen, White Blood Cell (WBC) count, partial thromboplastin time (PTT), Hemoglobin (HgB), hematocrit (hCT), Troponinl, Bilirubin total, Potassium, Magnesium, Lactate, Glucose, Bilirubin direct, Creatinine, Chloride, Calcium, Alkalinephos, blood urea nitrogen (BUN), aspartate aminotransferase (AST), arterial oxygenation (SaO2), partial pressure of carbon dioxide (PaCO2), potential of Hydrogen (pH), Fraction of inspired oxygen (FiO2), bicarbonate (HCO3) and BaseExcess. The demographic parameters (demographics in FIG. 2) typically include Age, Gender, Type of ICU, hospital admission duration and ICU stay duration.

In an embodiment of the present disclosure, the one or more processors 104, are configured to extract, at step 304, a plurality of discriminating features from the received test signals, wherein the plurality of discriminating features is a combination of continuous features and categorical features extracted during a training phase of at least one classifier. The extracting of discriminating features is explained in detail later in the description as part of the training phase.

In an embodiment of the present disclosure, the one or more processors 104, are configured to normalize, at step 306, the extracted plurality of discriminating features using stored values of standard deviation and mean associated with the one or more parameters from the training phase, wherein the normalizing is performed across sliding time windows. In an embodiment, the normalization is done according to the following equation:
$z_i = (x_i - x^-)/s$, wherein $x_i$ is a data point $(x_1, x_2, \ldots x_n)$, $x^-$ is a mean value and s is the standard deviation.

In an embodiment of the present disclosure, the one or more processors 104, are configured to rank, at step 308, the normalized extracted plurality of discriminating features using a Minimum Redundancy Maximum Relevance (MRMR) method to identify a subset (most relevant) of the plurality of discriminating features such that the subset is representative of a sepsis condition in the subject being monitored. The subset of the plurality of discriminating features extracted from the test signals is referred as testing data in the FIG. 2.

In an embodiment of the present disclosure, the one or more processors 104, are configured to predict, at step 310, a classification of the subject being monitored into one of a sepsis class and a normal class based on the identified subset using the at least one classifier trained during the training phase.

In an embodiment of the present disclosure, the training phase of the at least one classifier comprises receiving training signals corresponding to the one or more parameters, and wherein the training signals are obtained periodically from a plurality of subjects. In an embodiment, a dataset provided by M. Reyna Josef, et al., in "*Early prediction of sepsis from clinical data: the physionet/computing in cardiology challenge* 2019" referred hereinafter as the Physionet 2019 challenge dataset was used for the training signals. Hourly data consisting of 8 vital signals, 26 laboratory parameters and 6 demographic details of 40,336 subjects from two ICU units—Medical ICU (MICU) and Surgical ICU (SICU) were used in the training phase.

Figure 4:
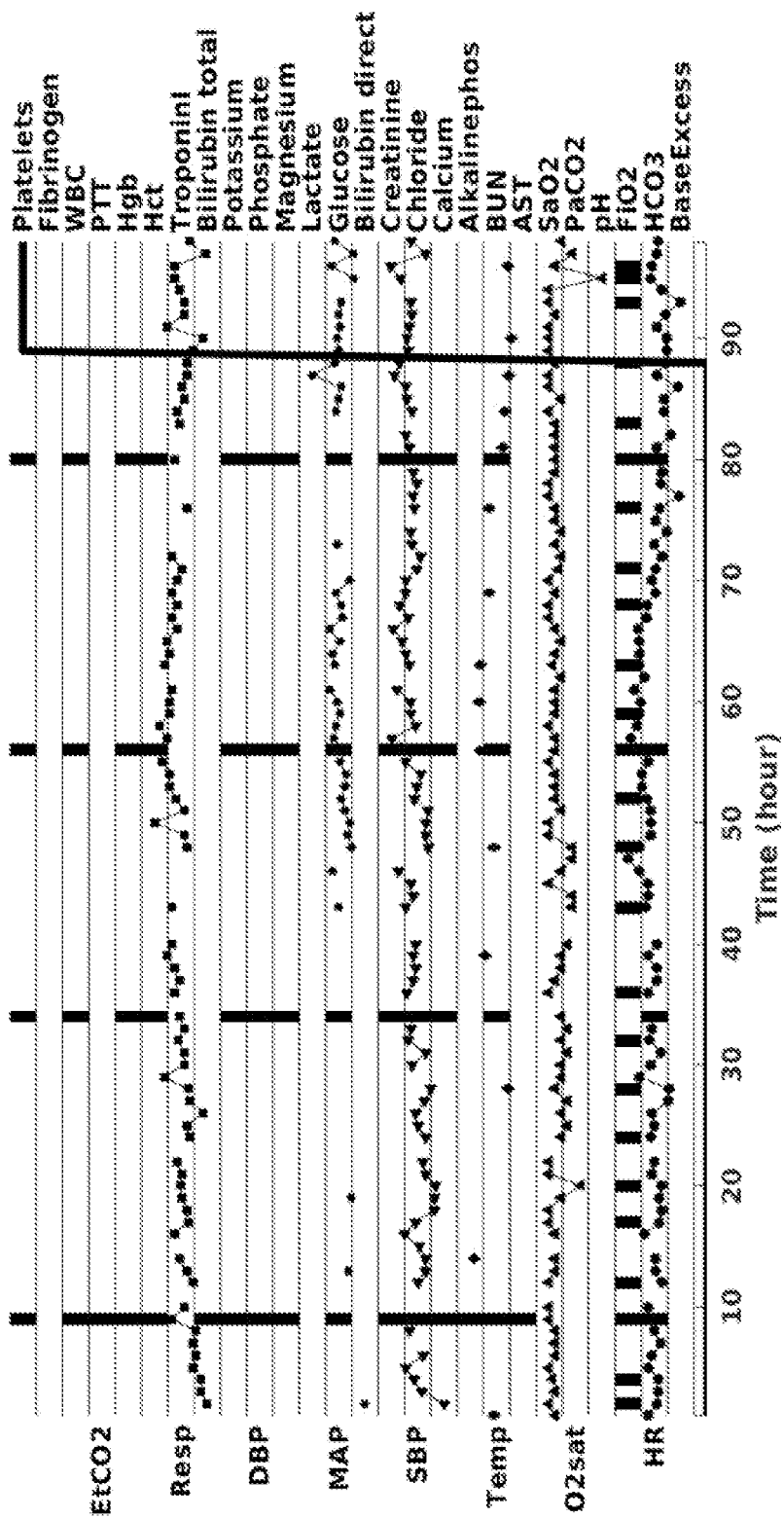
FIG. 4 illustrates a graphical representation of raw data for an Intensive Care Unit (ICU) patient transforming from a non-sepsis to a sepsis stage around $89^{th}$ hour of the patient's stay in a Medical ICU (MICU).

FIG. 4 illustrates a graphical representation, derived by the Applicant, of raw data (Physionet 2019 challenge dataset) for an ICU patient transforming from a non-sepsis to a sepsis stage around $89^{th}$ hour of the patient's stay in an MICU. Left vertical axis represents the vital signals and right vertical axis represents the laboratory parameters. Discontinuity in the vital parameters and the laboratory parameters indicate missing data indicative of the one or more parameters being sporadic in nature. Respective variation of the laboratory parameters is represented by bars (thick lines) where the shades are indicative of associated values (the higher the darker). In order to preserve the practicality of the problem at hand, Physionet Challenge 2019 organizers impose a restriction on analysis of the future data (which is practically not available for a subject being monitored). The present disclosure also imposes the same restriction i.e. "non-availability of future data at any given hour" during the training phase.

Figure 5:
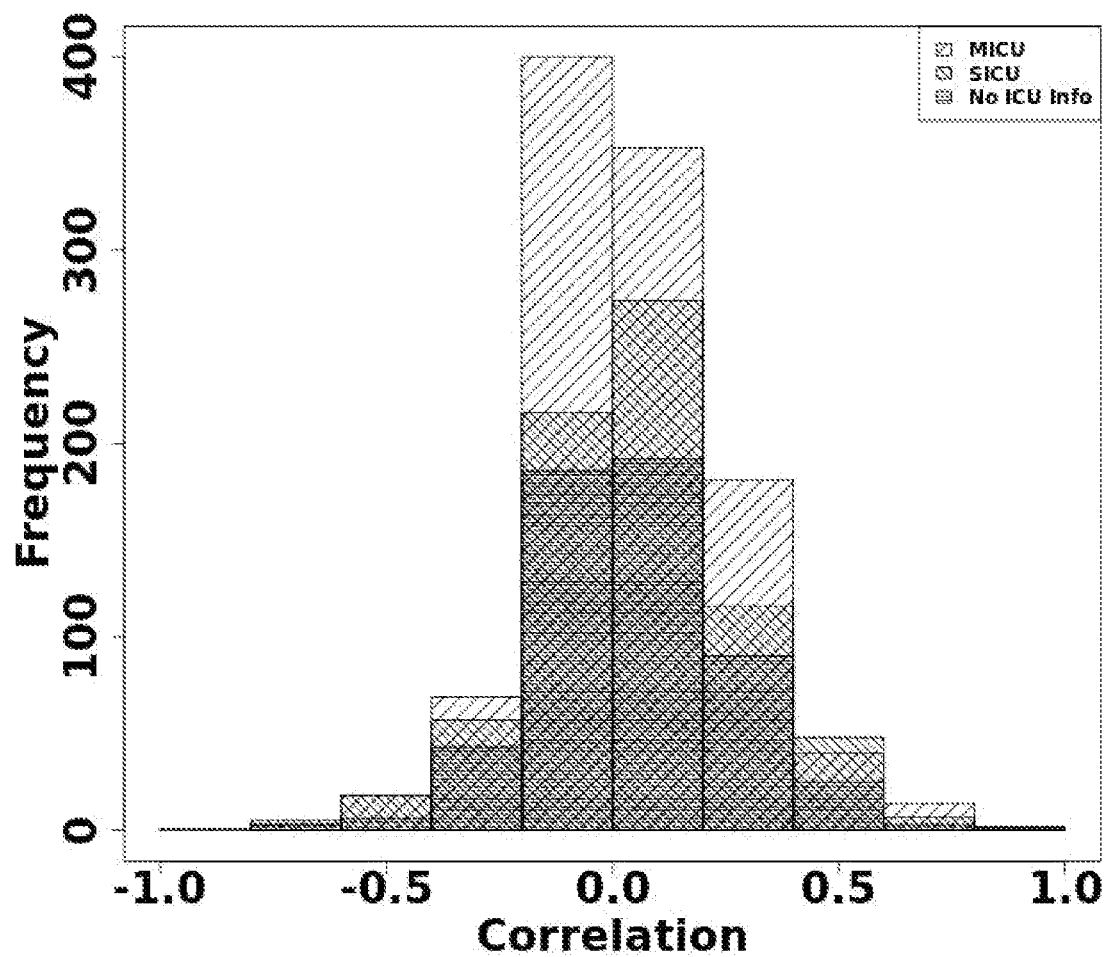
FIG. 5 illustrates a histogram of quick Sequential organ failure assessment (qSOFA) and Sepsis correlation for different ICUs.

Sequential organ failure assessment (SOFA) is a clinical prediction score used to track patient's status during the stay in ICU. SOFA score calculation requires information about the Hepato-renal function and Coagulatory status. quick Sequential organ failure assessment (qSOFA) is a simplified version of SOFA introduced by Sepsis-3 group in "The Third International Consensus Definitions for Sepsis and Septic Shock (Sepsis-3) Consensus Definitions for Sepsis and Septic Shock" by M. Singer et al. qSOFA requires only three parameters namely, Respiratory Rate (RR), Systolic Blood Pressure (SBP) and Glasgow Coma Scale (GCS). tSOFA is defined as a two-point change in the patients SOFA score. This along with clinical suspicion of infection helps in identifying potential for end-organ damage. The Physionet 2019 challenge dataset provides all parameters except GCS and Dopamine required for Nervous system and Cardiovascular system information respectively. Hence, both SOFA and qSOFA scores are approximated with the available parameters for all the patients at each hour and were correlated with the ground truth sepsis labels. FIG. 5 illustrates a histogram of quick Sequential organ failure assessment (qSOFA) and Sepsis correlation for different ICUs. As shown in FIG. 5, the correlation is extremely poor (peaked around zero). This may be attributed to the inconsistency in the Physionet 2019 challenge dataset. For instance, in the data represented in FIG. 4, Serum Bilirubin is an important indicator of hepatic function and is found missing in the Physionet 2019 challenge dataset.

Figure 6A:
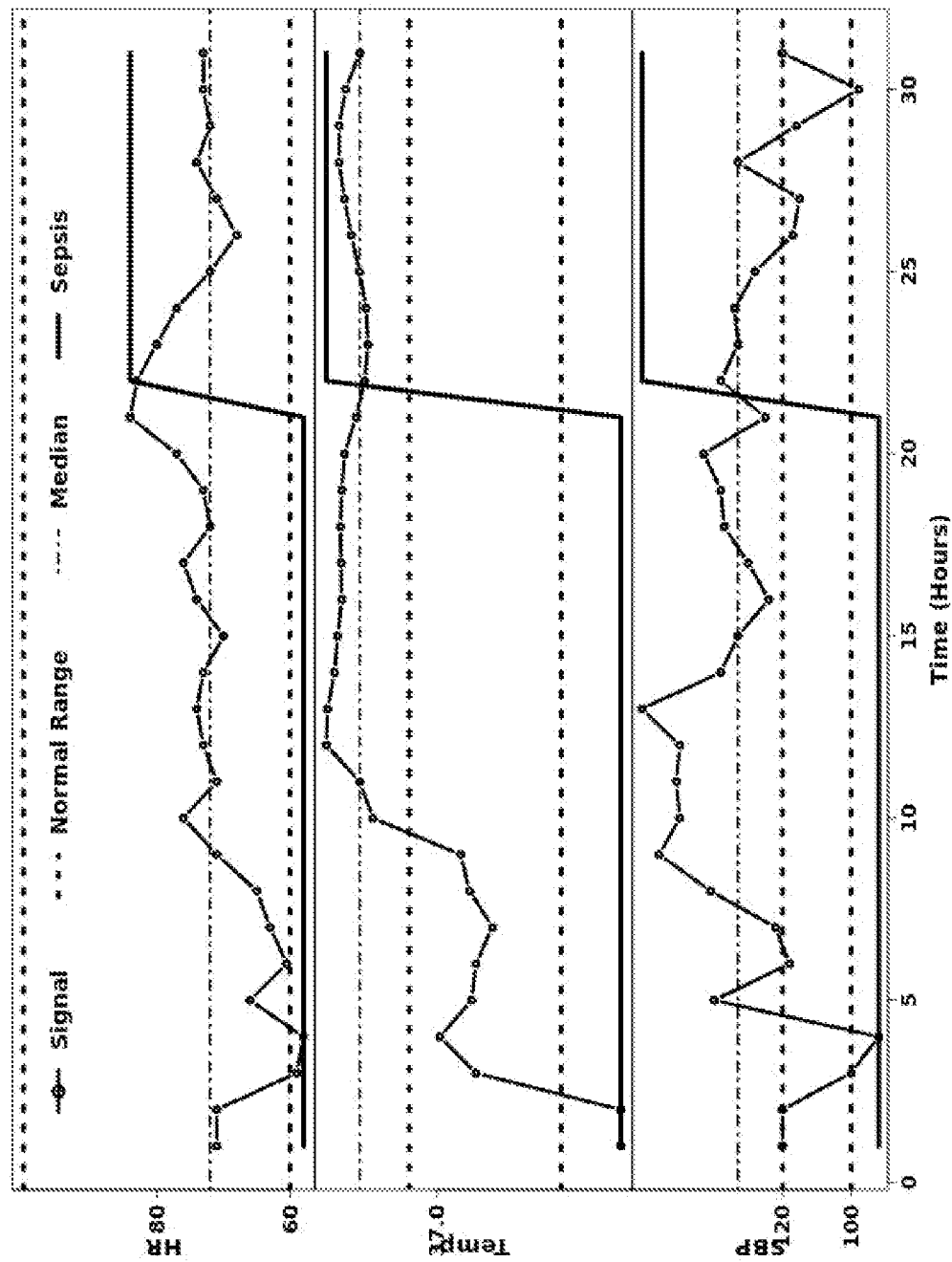
FIG. 6A and FIG. 6B illustrate a direct relation and an inverse relation respectively, between temperature and Systolic Blood Pressure (SBP).
Figure 6B:
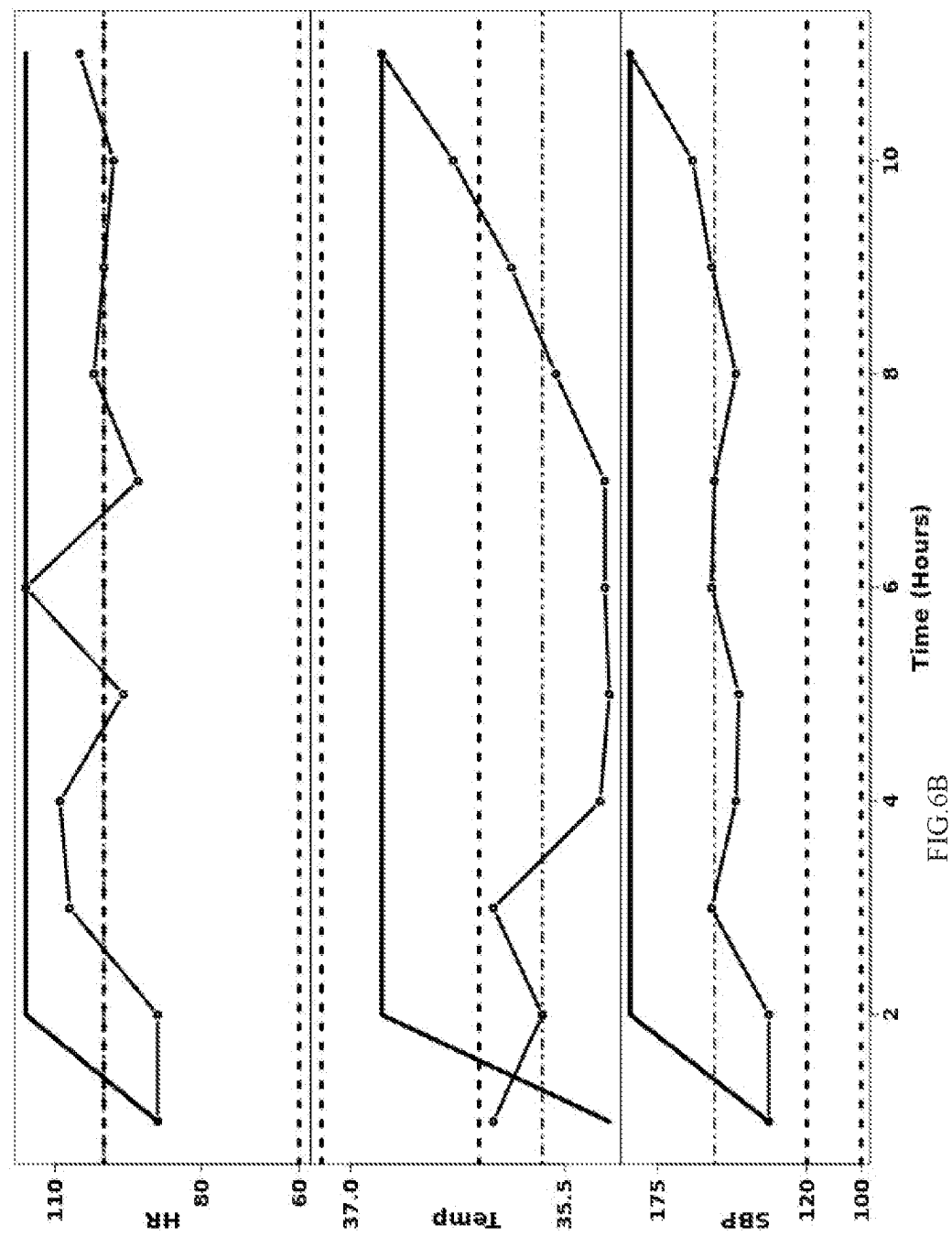

Abnormal HR is associated with sepsis. But when HR is within normal range (60-100), some relation is perceived between temperature and SBP. Both parameters are correlated bidirectionally (direct and inverse) with each other. FIG. 6A and FIG. 6B illustrate a direct relation and an inverse relation respectively, between temperature and Systolic Blood Pressure (SBP). When the temperature is lower than its normal range, there exists an inverse correlation between temperature and SBP (FIG. 6A). When the temperature is higher than its normal range, temperature and SBP exhibit a direct correlation (FIG. 66). This trend was noted visible in 70% of the subjects.

Figure 7:
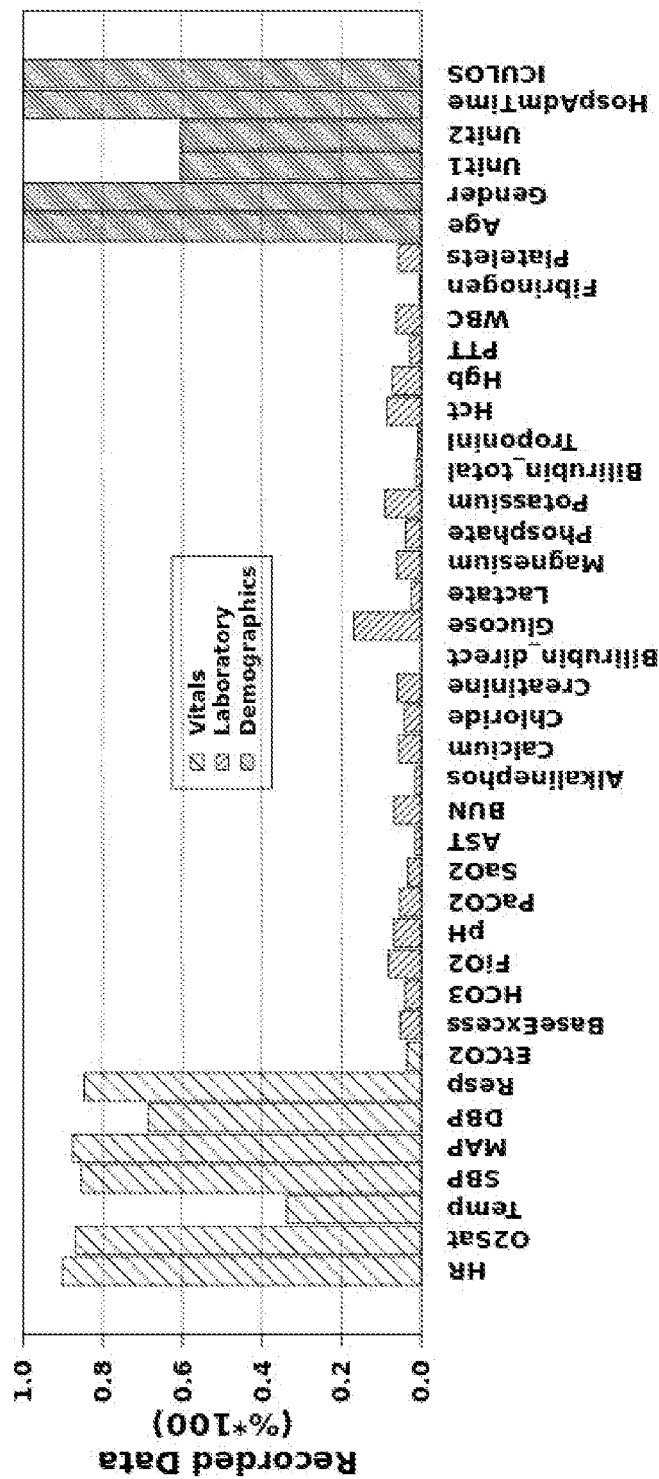
FIG. 7 illustrates a bar plot of the raw data showing missing data and inconsistency in the data.

Further, the Physionet 2019 challenge dataset was noted to be inconsistently inconsistent. There was no specific trend in missing data across the ICU stay of a subject as well as across subjects. The laboratory parameters are the most sporadic in nature. The vital signals, though measured more frequently, is far from a steady periodicity. FIG. 7 illustrates a bar plot of the raw data showing missing data and inconsistency in the data.

The Physionet 2019 challenge dataset was also noted to be highly imbalanced with 7.26% of the subjects heading to sepsis (2,932 out of 40,336). The sepsis occurrence in terms of hourly instances was much lower at 1.8%.

In an embodiment of the present disclosure, the training phase of the at least one classifier comprises extracting the plurality of discriminating features from the received training signals. In accordance with the present disclosure, 336 features were extracted from 34 signals (8 vitals and 26 laboratory) and 6 demographic parameters. Predominantly, variables or any observational data either represent measurements on some continuous scale, or they represent information about some categorical or discrete characteristics. In accordance with the present disclosure, the discriminating features include both the continuous features and the categorical features.

The continuous features: Sepsis progresses when the immune response to bacterial infection injures own tissues and organs. Given the fast progression of this medical condition, it is important to observe recent patient history over a time window (say i hours). For first i hours, the entire history available at that point of time is considered. i.e. the time window increases from $1^{st}$ hour to (i-1) hours. From the $i^{th}$ hour, a sliding time window of past (i-1) hours and the $i^{th}$ hour is considered for feature extraction. It is observed that the occurrence and/or frequency of lab tests are related with the progress of sepsis. For instance, in FIG. 4, during the initial hours, frequency of temperature measurement is low and after $56^{th}$ hour, it increases gradually till the patient is labeled sepsis in the $89^{th}$ hour. FIG. 4 also reveals that Mean Atrial Pressure (MAP) becomes more frequent after $48^{th}$ hour. A possible reason may be that depending on the current progression of sepsis in a subject, the physicians may decide to carry out certain procedures and/or administration of medicine(s). To measure the effect of those, they need to frequently monitor certain lab data. Hence, frequencies of lab tests become indirectly connected to sepsis progression.

Figure 9:
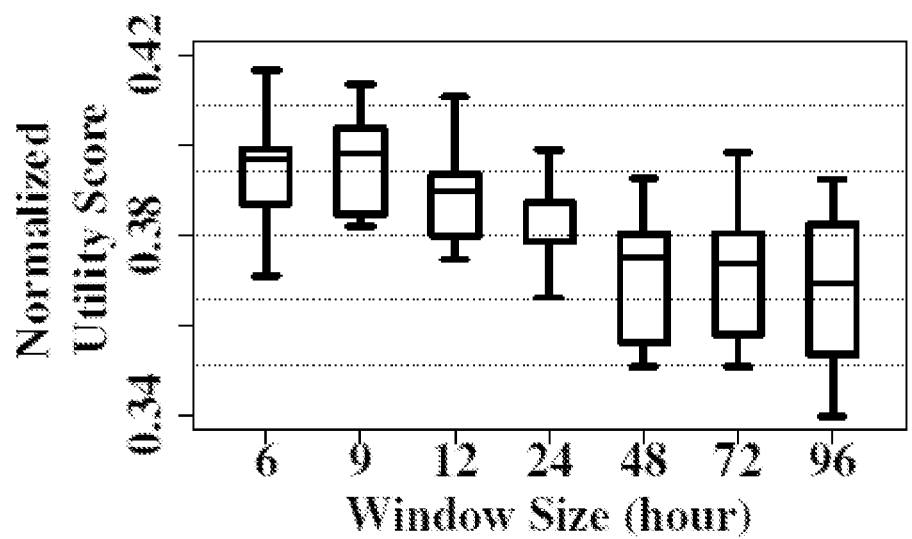
FIG. 9 illustrates a boxplot of a 5-fold utility score with variation of time window size, in accordance with some embodiments of the present disclosure.

In accordance with the present disclosure, the list of continuous features extracted from the 34 signals over an empirically determined sliding time window (i hours) are:
 a) count of valid data records associated with the one or more parameters;
 b) count of out of range data records associated with the one or more parameters;
 c) difference between a value associated with the one or more parameters at an $i^{th}$ hour and an $(i-1)^{th}$ hour;
 d) difference between a value associated with the one or more parameters at the $i^{th}$ hour and a mean of past $(i-1)$ hours; and
 e) difference between a value associated with the one or more parameters at the $i^{th}$ hour and a variance of the past $(i-1)$ hours;

In accordance with the present disclosure, i was varied from 6 to 96 hours to determine the sweet spot of the time window. FIG. 9 illustrates a boxplot of a 5-fold utility score with variation of time window size, in accordance with some embodiments of the present disclosure. It was observed that a sliding time window of 9 hours performs best. Accordingly, in an embodiment, the empirically determined sliding time window is 9 hours.

The categorical features: In accordance with the present disclosure, all 34 signals were considered as qualitative data and were binned into 6 categories. Then 4 features were extracted for each of the 34 signals resulting in 136 categorical features. In accordance with the present disclosure, the list of categorical features extracted from the 34 signals by using the binning approach are:
 a) Category;
 b) Upper limit (UL);
 c) Lower limit (LL); and
 d) One hot dummy encoding Table I provides the 6 categories and associated UL and LL for HR signal.

TABLE I

Categories for HR signal

| Input range | Category | UL | LL |
|---|---|---|---|
| 60-100 | 1 | 100 | 60 |
| 48-60 | 2 | 60 | 48 |
| 100-120 | 3 | 120 | 100 |
| 20-48 | 4 | 48 | 20 |
| 120-210 | 5 | 210 | 120 |
| NAN (Not A Number) | 6 | 0 | 0 |

Algorithm 1 below describes the categorical feature extraction from the training signals.

Algorithm 1: Categorical feature extraction using following limits: LL, UL, LL1 = 0.8 × LL, UL2 = 1.2 × UL

```
1.      procedure CATEGORICAL (LL, UL, LL2, UL2)
2.        switch S_i do
3.          case (LL_i < S_i < UL_i);
4.            return (1, LL_i, UL_i, 1);
5.          case (LL2_i < S_i < LL_i);
6.            return (2, LL2_i, LL_i, 1);
7.          case (UL_i < S_i < UL2_i);
8.            return (3, UL_i, UL2_i, 1);
9.          case (min (S_i) < S_i < LL2_i);
10.           return (4, min (S_i), LL2_i, 1);
11.         case (UL2_i < S_i < max (S_i));
12.           return (5, UL2_i, max (S_i), 1);
13.           case (S_i = NAN) return (6,0, 0, 0);
14.     end procedure
```

In Table II, few cases from HR were randomly chosen and the features were extracted using Algorithm 1 above. For instance, in case 1, HR is 70 beats per minute (bpm). Therefore, the category for 70 is '1', UL is '100' and LL is '60'. Table II provides the features extracted for sample HR cases.

TABLE II

Features extracted for sample HR cases

| | | Extracted Features | | | |
|---|---|---|---|---|---|
| Cases | HR | Category | UL | LL | One-hot |
| 1 | 70 | 1 | 100 | 60 | 1 |
| 2 | 45 | 4 | 48 | 20 | 1 |
| 3 | NAN | 6 | 0 | 0 | 0 |
| 4 | 110 | 3 | 100 | 100 | 1 |

The categorical features corresponding to demography: In accordance with the present disclosure, following features were extracted:
 a) Current hospital admission duration;
 b) Intensive Care Unit (ICU) type (MICU or SICU);
 c) Gender;
 d) Age binned in empirically determined categories of ranges of the age;
 e) Current ICU stay duration binned in steps of empirically determined hours;
 f) The LL of current ICU stay duration;
 g) The UL of current ICU stay duration;
 h) The LL of age; and
 i) The UL of age;

In an embodiment, the ICU stay duration is divided into non-overlapping bins of 10 hours along with their LL and UL. For e.g. <10 hours, 10-20 hours, 21-30 hours, etc. If the current ICU stay is 28, it is placed in the bin 21-30 hours with 20 as the LL and 30 as the UL. Similarly, in an embodiment, the empirically determined categories of ranges of the age is 4 categories, 0-25, 25-50, 50-75 and 75-100 years along with their LL and UL.

The categorical features corresponding to a sepsis domain: In accordance with the present disclosure, following features were extracted:
 a) National Early Warning Score (NEWS);
 b) Modified Early Warning Score (MEWS); and
 c) Acute Physiology and Chronic Health Evaluation II (APACHE II).

Since the Physionet 2019 challenge dataset has missing data such as level of consciousness and emergency oxygen therapy information—awareness, verbal and painful response, etc., only signals available in the dataset were selected and separate categories were made which yielded 21 features.

Figure 8:
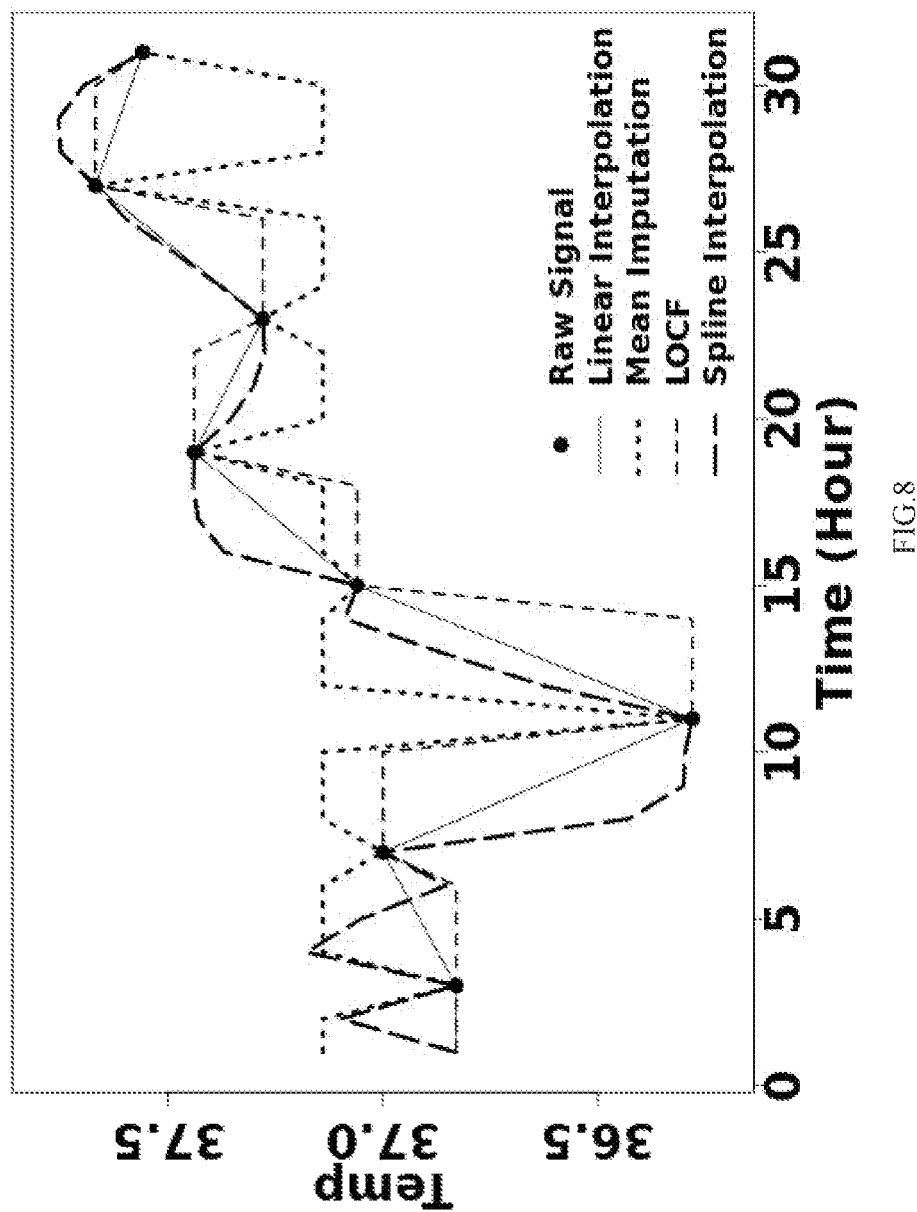
FIG. 8 illustrates a comparison of data imputation methods when used, in accordance with some embodiments of the present disclosure.

In accordance with an embodiment of the present disclosure, the step of extracting the plurality of discriminating features from the received test signals (304) or the received training signals are both preceded by preprocessing the received test signals or the received training signals respectively, by imputing the missing data. In an embodiment, the preprocessing methods may include Last Observation Carried Forward (LOCF), Next Observation Carried Backward (NOCB), mean imputation and interpolation techniques. FIG. 8 illustrates a comparison of data imputation methods when used, in accordance with some embodiments of the present disclosure. LOCF and NOCB are statistical approaches to the analyses of longitudinal data where some follow-up observations may be missing. Longitudinal data tracks the same sample at different points in time. Computing the overall mean is an imputation method that takes no precedence of the time series characteristics or relationship between the variables. In accordance with the present disclosure, interpolation is performed on all the 8 vital signals by fitting spline/linear if at least two values are present. In case, there exits only one value in the entire signal, the same value is repeated for the rest of the ICU stay and if there exists no value for the entire signal, random values within the normal range are taken. Ranges for these random values are selected such that variation between them is less.

Data imputation was performed subject-wise in the training phase and time window-wise for the testing signals associated with the subject being monitored.

TABLE III (Normalized utility scores) × $10^{-3}$ after preprocessing with median value in bold text.

| Imputation method | Five-folds | | | | | |
|---|---|---|---|---|---|---|
| | 1 | 2 | 3 | 4 | 5 | Variance |
| LOCF & NOCB | 169 | 181 | 175 | 187 | 144 | 276 |
| Mean | 142 | 184 | 176 | 193 | 110 | 1185 |
| Spline | 186 | 211 | 213 | 208 | 251 | 550 |
| Linear | 192 | 209 | 220 | 220 | 163 | 578 |

It is observed from Table III that all imputation methods introduce bias in analysis and perform poorly for the Physionet 2019 challenge dataset. However, the preprocessing may be considered for other training signals. One possible reason for the poor performance may be the unknown activities in ICUs. For instance, a lot of medicines and external fluid get administered, other body conditions (fasting for some tests etc.) are imposed. Without these details, in a sporadic dataset, imputation is incomplete, resulting in lowering Signal to Noise Ratio (SNR) in the imputed signal.

Figure 10:
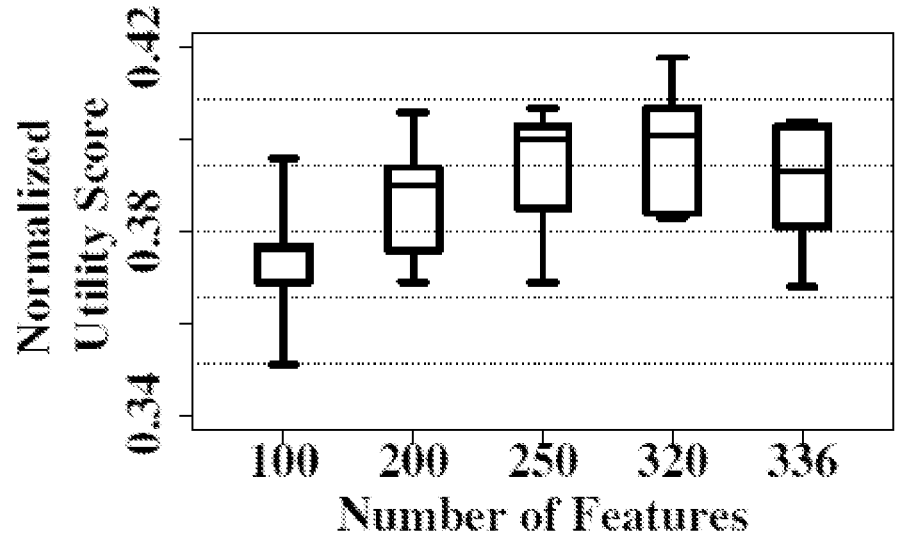
FIG. 10 illustrates a boxplot of a 5-fold utility score using a subset of discriminative features, in accordance with some embodiments of the present disclosure.

Once the plurality of discriminating features are extracted from the training signals, in an embodiment of the present disclosure, the training phase of the at least one classifier further comprises normalizing the extracted plurality of discriminating features using values of standard deviation and mean associated with the one or more parameters, wherein the normalizing is performed across the plurality of subjects of the Physionet 2019 challenge dataset. The normalized extracted plurality of discriminating features is then ranked using the MRMR method to identify the subset (relevant) of the plurality of discriminating features. The subset of the plurality of discriminating features extracted from the training signals is referred as training data in the FIG. 2. FIG. 10 illustrates a boxplot of a 5-fold utility score using a subset of discriminative features, in accordance with some embodiments of the present disclosure. Cross validation performance with increasing number of ranked features may be observed in FIG. 10. High bias, low variance combination, i.e. the box having least stretch, high minimum and high median value is selected. FIG. 10 shows the top 320 features provide an optimal performance. The most prominent features as shown in Table IV are selected from the different categories, thereby validating the differentiating nature of the features extracted.

TABLE IV

List of 10 features (subset of the extracted features) selected by the MRMR method.

| Features (1-5) | Features (6-10) |
|---|---|
| ICU stay | $i^{th}$ - $(i-1)^{th}$ hour of O2sat |
| Non-NAN count of FiO2 | Out of Range of WBC |
| NEWS cutoff for HR | Out of Range of PTT |
| $i^{th}$ - $(i-1)^{th}$ hour of SaO2 | Hospital admission duration |
| Category of RR | Category of glucose |

To balance the sepsis class and the normal class in the received training signals, a majority class (typically the normal class) is under-sampled. The at least one classifier is finally trained using the identified subset corresponding to the balanced sepsis class and the normal class.

In accordance with an embodiment of the present disclosure, the at least one classifier includes at least one of a Random Forest (RF) model and an Adaptive Logistic Regression of Ensemble learning (LB) model. Hyper parameters of both the models are tuned by Bayesian optimization considering the error of median of a Normalized Utility Score (NUS) as the minimizing optimization function.

In an embodiment of the present disclosure, the one or more processors 104, are configured to obtain, at step 312, a final class of the subject being monitored by fusing predictions by the RF model and the LB model using one or more logical operations. In an embodiment of the present disclosure, conjunction operation is used.

To demonstrate the potential efficacy of the features considered in the present disclosure, a 5-fold cross-validation was performed on all the time windows (multiple time windows were extracted from each subject. In order to avoid over-fitting, the partitions for cross-validation were done in such a manner that windows from the same subject never appear in both the training signals and testing signals data. The function for calculating the NUS generously rewards the at least one classifier for initial predictions of sepsis and penalizes it for late or missed predictions. According to an evaluation function, the at least one classifier is rewarded when sepsis forecast lies between 12 hours before and 3 hours after $t_{sepsis}$ (onset time of sepsis). Sepsis labels are already shifted ahead by 6 hours in the data. They are shifted ahead again by 6 hours in the training signal data for optimal prediction. The performance evaluations are provided for various baselines in Table V with highlighted median values.

The baselines referred are as follows:

Baseline 1: the continuous features associated with the one or more parameters being the physiological parameters and the laboratory parameters over an empirically determined sliding time window (i hours) used with the RF classifier.

Baseline 2: the features of Baseline 1 used with the categorical features by using a binning approach on the one or more parameters being the physiological parameters and the laboratory parameters and the RF classifier.

Baseline 3: the features of Baseline 1, the features of Baseline 2 and the categorical features corresponding to demography used with the RF classifier.

Baseline 4: the features of Baseline 1, the features of Baseline 2, the features of Baseline 3 and the categorical features corresponding to a sepsis domain used with the RF classifier.

Baseline 5: the features of Baseline 1, the features of Baseline 2, the features of Baseline 3 and the categorical features corresponding to a sepsis domain used with the LB classifier.

Baseline 6: the features of Baseline 1, the features of Baseline 2, the features of Baseline 3 and the categorical features corresponding to a sepsis domain used with the RF classifier and the LB classifier.

TABLE V

Performance comparison for all baselines above

| Baselines | NUS × $10^{-3}$ for 5 folds | | | | | |
|---|---|---|---|---|---|---|
| | 1 | 2 | 3 | 4 | 5 | Variance |
| 1 | 225 | 250 | 242 | 248 | 230 | 122 |
| 2 | 230 | 286 | 272 | 281 | 241 | 626 |
| 3 | 356 | 384 | 363 | 371 | 331 | 390 |
| 4 | 359 | 387 | 370 | 378 | 343 | 292 |
| 5 | 374 | 397 | 395 | 387 | 371 | 141 |
| 6 | 383 | 418 | 401 | 407 | 384 | 227 |

A gradual improvement in median was observed as features were added while moving to higher baselines. The same was not observed for the variance parameter. As noted from Table V from the performance of the baselines 4, 5 and 6, the LB classifier provides two-fold improvement—reducing variation as well improving bias over the RF classifier. This may be due to the high dimension of features. The fusing of predictions by the RF model and the LB model in the Baseline 6 provides further improvement in bias in each fold, but the percentage of improvement was not uniform throughout all the folds, resulting into increase in variance.

Sepsis is one of the leading life-threatening bacterial and viral infections that often turns fatal if not detected and treated in time. Each hour of delayed treatment leads to 4-8% increase in mortality rate. Based on the above description and the experimental evaluations of the approach of the present disclosure, it may be concluded that the methods and systems of the present disclosure enable early detection of sepsis by providing discriminating features and a pipeline depicted in FIG. 2 and further described as the method 300, leading to a life-saving tool.

In an embodiment of the present disclosure, the one or more processors 104, are configured to administer, at step 314, antibiotics to the subject being predicted as belonging to the class sepsis.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising the steps of:
   receiving, via one or more hardware processors, test signals corresponding to one or more parameters, wherein the one or more parameters include physiological parameters, laboratory parameters and demographic parameters, and wherein the test signals are obtained periodically from a subject being monitored, wherein the subject is housed in an intensive care unit (ICU);
   pre-processing, via one or more hardware processors, the received test signals by imputing missing data using at least one of Last Observation Carried Forward (LOCF), Next Observation Carried Backward (NOCB), mean imputation, and interpolation techniques, wherein the imputation of the missing data is performed subject-wise in a training phase of at least one classifier and time window-wise for the received test signals associated with the subject being monitored;
   extracting, via the one or more hardware processors, a plurality of discriminating features from the received test signals, wherein the plurality of discriminating features is a combination of continuous features and categorical features extracted during the training phase of the at least one classifier, wherein the plurality of discriminating features comprises:
   (i) the continuous features associated with the one or more parameters being the physiological parameters and the laboratory parameters over an empirically determined sliding time window (i hours);
   (ii) the categorical features by using a binning approach on the one or more parameters being the physiological parameters and the laboratory parameters;
   (iii) the categorical features corresponding to the demographic parameters; and
   (iv) the categorical features corresponding to a sepsis domain;
   normalizing, via the one or more hardware processors, the extracted plurality of discriminating features using stored values of standard deviation and mean associated with the one or more parameters from the training phase, wherein the normalizing is performed across sliding time windows;
   ranking, via the one or more hardware processors, the normalized extracted plurality of discriminating features using a Minimum Redundancy Maximum Relevance (MRMR) method to identify a subset of the plurality of discriminating features such that the subset is representative of a sepsis condition in the subject being monitored; and
   predicting, via the one or more hardware processors, a classification of the subject being monitored into one of a sepsis class and a normal class based on the identified subset using the at least one classifier trained during the training phase.

2. The processor implemented method of claim 1, wherein the training phase of the at least one classifier comprises:
   receiving training signals corresponding to the one or more parameters, and wherein the training signals are obtained periodically from a plurality of subjects;
   extracting the plurality of discriminating features from the received training signals;
   normalizing the extracted plurality of discriminating features using values of standard deviation and mean associated with the one or more parameters, wherein the normalizing is performed across the plurality of subjects;
   ranking the normalized extracted plurality of discriminating features using the MRMR method to identify the subset of the plurality of discriminating features;
   under-sampling a majority class to balance the sepsis class and the normal class in the received training signals; and
   training the at least one classifier using the identified subset corresponding to the balanced sepsis class and the normal class.

3. The processor implemented method of claim 2, wherein the step of extracting the plurality of discriminating features from the received training signals is preceded by preprocessing the received training signals by imputing missing data therein.

4. The processor implemented method of claim 2, wherein the at least one classifier includes at least one of a Random Forest (RF) model and an Adaptive Logistic Regression of Ensemble learning (LB) model.

5. The processor implemented method of claim 1, wherein the plurality of discriminating features comprises:
   (i) the continuous features associated with the one or more parameters being the physiological parameters and the laboratory parameters over the empirically determined sliding time window (i hours) including:
      a) count of valid data records associated with the one or more parameters;
      b) count of out of range data records associated with the one or more parameters;
      c) difference between a value associated with the one or more parameters at an $i^{th}$ hour and an $(i-1)^{th}$ hour;
      d) difference between a value associated with the one or more parameters at the $i^{th}$ hour and a mean of past (i−1) hours; and
      e) difference between a value associated with the one or more parameters at the $i^{th}$ hour and a variance of the past (i−1) hours;
   (ii) the categorical features by using the binning approach on the one or more parameters being the physiological parameters and the laboratory parameters including:
      a) Category;
      b) Upper limit (UL);
      c) Lower limit (LL); and
      d) One hot dummy encoding;
   (iii) the categorical features corresponding to the demographic parameters including:
      a) Current hospital admission duration;
      b) Intensive Care Unit (ICU) type;
      c) Gender;
      d) Age binned in empirically determined categories of ranges of the age;
      e) Current ICU stay duration binned in steps of empirically determined hours;
      f) The LL of current ICU stay duration;
      g) The UL of current ICU stay duration;
      h) The LL of age; and
      i) The UL of age; and (iv) the categorical features corresponding to the sepsis domain including:
  a) National Early Warning Score (NEWS);
  b) Modified Early Warning Score (MEWS); and
  c) Acute Physiology and Chronic Health Evaluation II (APACHE II).

6. The processor implemented method of 4, further comprising obtaining a final class of the subject being monitored by fusing predictions by the RF model and the LB model using one or more logical operations.

7. The processor implemented method of 6, further comprising administering antibiotics to the subject being predicted as belonging to the class sepsis.

8. A system comprising:
one or more data storage devices operatively coupled to one or more hardware processors and configured to store instructions configured for execution via the one or more hardware processors to:
  receive test signals corresponding to one or more parameters, wherein the one or more parameters include physiological parameters, laboratory parameters and demographic parameters, and wherein the test signals are obtained periodically from a subject being monitored, wherein the subject is housed in an intensive care unit (ICU);
  pre process the received test signals by imputing missing data using at least one of Last Observation Carried Forward (LOCF), Next Observation Carried Backward (NOCB), mean imputation, and interpolation techniques, wherein the imputation of the missing data is performed subject-wise in a training phase of at least one classifier and time window-wise for the received test signals associated with the subject being monitored;
  extract a plurality of discriminating features from the received test signals, wherein the plurality of discriminating features is a combination of continuous features and categorical features extracted during the training phase of the at least one classifier, wherein the plurality of discriminating features comprises:
    (i) the continuous features associated with the one or more parameters being the physiological parameters and the laboratory parameters over an empirically determined sliding time window (i hours);
    (ii) the categorical features by using a binning approach on the one or more parameters being the physiological parameters and the laboratory parameters;
    (iii) the categorical features corresponding to the demographic parameters; and
    (iv) the categorical features corresponding to a sepsis domain;
  normalize the extracted plurality of discriminating features using stored values of standard deviation and mean associated with the one or more parameters from the training phase, wherein the normalizing is performed across sliding time windows;
  rank the normalized extracted plurality of discriminating features using a Minimum Redundancy Maximum Relevance (MRMR) method to identify a subset of the plurality of discriminating features such that the subset is representative of a sepsis condition in the subject being monitored; and
  predict a classification of the subject being monitored into one of a sepsis class and a normal class based on the identified subset using the at least one classifier trained during the training phase.

9. The system of claim 8, wherein the one or more processors are further configured to perform, during the training phase of the at least one classifier, steps comprising:
  receiving training signals corresponding to the one or more parameters, and wherein the training signals are obtained periodically from a plurality of subjects;
  extracting the plurality of discriminating features from the received training signals;
  normalizing the extracted plurality of discriminating features using values of standard deviation and mean associated with the one or more parameters, wherein the normalizing is performed across the plurality of subjects;
  ranking the normalized extracted plurality of discriminating features using the MRMR method to identify the subset of the plurality of discriminating features;
  under-sampling a majority class to balance the sepsis class and the normal class in the received training signals; and
  training the at least one classifier using the identified subset corresponding to the balanced sepsis class and the normal class.

10. The system of claim 9, wherein the one or more processors are further configured to preprocess the received training signals by imputing missing data therein before extracting the plurality of discriminating features from the received training signals.

11. The system of claim 9, wherein the at least one classifier includes at least one of a Random Forest (RF) model and an Adaptive Logistic Regression of Ensemble learning (LB) model.

12. The system of claim 8, wherein the plurality of discriminating features comprises:
  (i) the continuous features associated with the one or more parameters being the physiological parameters and the laboratory parameters over the empirically determined sliding time window (i hours) including:
    a) count of valid data records associated with the one or more parameters;
    b) count of out of range data records associated with the one or more parameters;
    c) difference between a value associated with the one or more parameters at an $i^{th}$ hour and an $(i-1)^{th}$ hour;
    d) difference between a value associated with the one or more parameters at the $i^{th}$ hour and a mean of past $(i-1)$ hours; and
    e) difference between a value associated with the one or more parameters at the $i^{th}$ hour and a variance of the past $(i-1)$ hours;
  (ii) the categorical features by using the binning approach on the one or more parameters being the physiological parameters and the laboratory parameters including:
    a) Category;
    b) Upper limit (UL);
    c) Lower limit (LL); and
    d) One hot dummy encoding;
  (iii) The categorical features corresponding to the demographic parameters including:
    a) Current hospital admission duration;
    b) Intensive Care Unit (ICU) type;
    c) Gender;
    d) Age binned in empirically determined categories of ranges of the age;
    e) Current ICU stay duration binned in steps of empirically determined hours;
    f) The LL of current ICU stay duration;
    g) The UL of current ICU stay duration;

h) The LL of age; and
i) The UL of age; and
(iv) the categorical features corresponding to the sepsis domain including:
a) National Early Warning Score (NEWS);
b) Modified Early Warning Score (MEWS); and
c) Acute Physiology and Chronic Health Evaluation II (APACHE II).

13. The system of claim 11, wherein the one or more processors are further configured to obtain a final class of the subject being monitored by fusing predictions by the RF model and the LB model using one or more logical operations.

14. The system of claim 13, wherein the one or more processors are further configured to administer antibiotics to the subject being predicted as belonging to the class sepsis.

15. A computer program product comprising a non-transitory computer readable medium having a computer readable program embodied therein, wherein the computer readable program, when executed on a computing device, causes the computing device to:
receive test signals corresponding to one or more parameters, wherein the one or more parameters include physiological parameters, laboratory parameters and demographic parameters, and wherein the test signals are obtained periodically from a subject being monitored, wherein the subject is housed in an intensive care unit (ICU);
pre-process the received test signals by imputing missing data using at least one of Last Observation Carried Forward (LOCF), Next Observation Carried Backward (NOCB), mean imputation, and interpolation techniques, wherein the imputation of the missing data is performed subject-wise in a training phase of at least one classifier and time window-wise for the received test signals associated with the subject being monitored;
extract a plurality of discriminating features from the received test signals, wherein the plurality of discriminating features is a combination of continuous features and categorical features extracted during the training phase of the at least one classifier, wherein the plurality of discriminating features comprises:
(i) the continuous features associated with the one or more parameters being the physiological parameters and the laboratory parameters over an empirically determined sliding time window (i hours);
(ii) the categorical features by using a binning approach on the one or more parameters being the physiological parameters and the laboratory parameters;
(iii) the categorical features corresponding to the demographic parameters; and
(iv) the categorical features corresponding to a sepsis domain;
normalize the extracted plurality of discriminating features using stored values of standard deviation and mean associated with the one or more parameters from the training phase, wherein the normalizing is performed across sliding time windows;
rank the normalized extracted plurality of discriminating features using a Minimum Redundancy Maximum Relevance (MRMR) method to identify a subset of the plurality of discriminating features such that the subset is representative of a sepsis condition in the subject being monitored; and
predict a classification of the subject being monitored into one of a sepsis class and a normal class based on the identified subset using the at least one classifier trained during the training phase.

16. The computer program product of claim 15, wherein the computer readable program further causes the computing device to perform, during the training phase of the at least one classifier, steps comprising:
receiving training signals corresponding to the one or more parameters, and wherein the training signals are obtained periodically from a plurality of subjects;
extracting the plurality of discriminating features from the received training signals;
normalizing the extracted plurality of discriminating features using values of standard deviation and mean associated with the one or more parameters, wherein the normalizing is performed across the plurality of subjects;
ranking the normalized extracted plurality of discriminating features using the MRMR method to identify the subset of the plurality of discriminating features;
under-sampling a majority class to balance the sepsis class and the normal class in the received training signals; and
training the at least one classifier using the identified subset corresponding to the balanced sepsis class and the normal class.

17. The computer program product of claim 16, wherein the computer readable program further causes the computing device to obtain a final class of the subject being monitored by fusing predictions by the at least one classifier being at least one of a Random Forest (RF) model and an Adaptive Logistic Regression of Ensemble learning (LB) model using one or more logical operations.

* * * * *